United States Patent
Rogers et al.

(10) Patent No.: US 11,881,298 B2
(45) Date of Patent: Jan. 23, 2024

(54) SYSTEMS AND METHODS FOR UNIVERSAL ARTIFICIAL INTELLIGENCE INTEGRATION SERVICES

(71) Applicant: GE Precision Healthcare LLC, Milwaukee, WI (US)

(72) Inventors: Garrett Rogers, Channahon, IL (US); Kunal Patil, Aurora, IL (US); Pankaj Kumar, Chicago, IL (US); Mayuri Kumari, Chicago, IL (US); Arun Viswanath, Barrington, IL (US); Vijay Kumar Reddy Arlagadda, Hoffman Estates, IL (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 359 days.

(21) Appl. No.: 17/229,670

(22) Filed: Apr. 13, 2021

(65) Prior Publication Data

US 2022/0328164 A1    Oct. 13, 2022

(51) Int. Cl.
*G16H 30/20*      (2018.01)
*G06N 20/00*      (2019.01)
*G16H 80/00*      (2018.01)
*G16H 10/60*      (2018.01)

(52) U.S. Cl.
CPC .............. *G16H 30/20* (2018.01); *G06N 20/00* (2019.01); *G16H 10/60* (2018.01); *G16H 80/00* (2018.01)

(58) Field of Classification Search
CPC ........ G16H 30/20; G16H 10/60; G16H 80/00; G16H 40/20; G16H 30/40; G06N 20/00
See application file for complete search history.

(56) References Cited

U.S. PATENT DOCUMENTS

| 11,664,111 B2* | 5/2023 | Mankovich | G16H 40/63 |
| | | | 715/768 |
| 2018/0137244 A1* | 5/2018 | Sorenson | G16H 30/20 |
| 2020/0167373 A1* | 5/2020 | Siddiqui | H04L 67/561 |
| 2020/0311938 A1* | 10/2020 | Vincent | G16H 80/00 |
| 2021/0174941 A1* | 6/2021 | Mathur | H04L 63/102 |
| 2021/0398650 A1* | 12/2021 | Baker | A61B 6/5294 |

FOREIGN PATENT DOCUMENTS

WO    WO-2021046241 A1 *   3/2021     G06K 9/6262

OTHER PUBLICATIONS

Korenblum et al., Managing Biomedical Image Metadata for Search and Retrieval of Similar Images, Aug. 2011, Journal of Digital Imaging, vol. 24, No. 4, pp. 739-748. (Year: 2011).*

* cited by examiner

*Primary Examiner* — Christopher L Gilligan
*Assistant Examiner* — C. Luke Gilligan
(74) *Attorney, Agent, or Firm* — McCoy Russell LLP (57) ABSTRACT

Systems and methods are provided for integrating artificial intelligence (AI) workflows. In one example, a method includes receiving, from a medical image storage device, an instance availability notification, in response to determining that the notification indicates that one or more medical images have been saved at the medical image storage device, querying the medical image storage device to retrieve metadata associated with the one or more medical images, initiating a work-item with an AI orchestration platform for the metadata, and receiving, from the AI orchestration platform via the work-item, AI results related to the one or more medical images.

19 Claims, 6 Drawing Sheets

SYSTEMS AND METHODS FOR UNIVERSAL ARTIFICIAL INTELLIGENCE INTEGRATION SERVICES

FIELD

Embodiments of the subject matter disclosed herein relate to artificial intelligence (AI) workflows, and more particularly to a workflow repository and engine between a medical image storage device and an AI orchestration platform.

BACKGROUND

Healthcare facilities often employ certain types of medical imaging modalities, such as computed tomography, magnetic resonance imaging, ultrasound imaging, and X-ray imaging. These medical imaging modalities use a common format for image data, known as digital imaging and communications in medicine (DICOM). The evolution of the DICOM format facilitated the development and expansion of picture archiving and communication systems (PACS). To facilitate in generating clinical findings via medical images or other tasks, the PACS may communicate with an artificial intelligence (AI) orchestration platform (AOP), which is configured to execute multiple AI models against any given number of datasets.

BRIEF DESCRIPTION

In one aspect, a method includes receiving, from a medical image storage device, an instance availability notification; in response to determining that the notification indicates that one or more medical images have been saved at the medical image storage device, querying the medical image storage device to retrieve metadata associated with the one or more medical images; initiating a workitem with an AI orchestration platform for the metadata; and receiving, from the AI orchestration platform via the work-item, AI results related to the one or more medical images.

In another aspect, a system includes a medical image storage device communicatively coupled to a plurality of medical imaging devices, the medical image storage device configured to store medical images acquired via the plurality of medical imaging devices; an artificial intelligence (AI) server communicatively coupled to the medical image storage device, the AI server comprising a processor and a non-transitory memory storing a plurality of AI models; and an AI integration server communicatively coupled to the medical image storage device and the AI server. The AI integration server includes a processor and a non-transitory memory storing a datastore for output of the plurality of AI models. The AI integration server is further configured with executable instructions stored in the non-transitory memory that when executed cause the processor to: receive, from the medical image storage device, an instance availability notification indicating that one or more medical images have been saved at the medical image storage device; retrieve, from the medical image storage device, metadata relating to the one or more medical images responsive to the instance availability notification; transmit, to the AI server, a request including the metadata relating to the one or more medical images; receive, from the AI server, AI results generated by one or more of the plurality of AI models for the one or more medical images; and store the AI results for the one or more medical images in the datastore.

In a still further aspect, a system includes an artificial intelligence (AI) integration server communicatively coupled to a medical image storage device and an AI server storing a plurality of AI models, the AI integration server comprising a processor and a non-transitory memory storing a datastore for output of the plurality of AI models. The AI integration server is configured with executable instructions stored in the non-transitory memory that when executed cause the processor to: receive, from the AI server, AI results generated by one or more of the plurality of AI models for one or more medical images stored at the medical image storage device; store the AI results for the one or more medical images in the datastore; receive, from an end user application, a notification that an end user has rejected the one or more medical images, and discard the AI results responsive to the notification; and control the medical image storage device to discard any data objects related to the AI results stored at the medical image storage device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of a universal artificial intelligence (AI) integration service (referred to herein as a UAIS or an AI integration server) configured to implement a workflow repository and engine between a medical image storage device, such as a picture archiving and communication system (PACS) or a vendor neutral archive (VNA), and one or more external servers. The medical image storage device (e.g., the PACS and/or VNA) is configured to receive, store, and send medical images and other data according to the digital imaging and communications in medicine (DICOM) standard. Thus, the medical image storage device may be limited in the functionalities that may be provided by the medical image storage device, as the medical image storage device may not execute any programs or applications that are not covered by or allowed by the DICOM standard. As such, various external devices may be integrated with the medical image storage device to expand the functionality of the medical image storage device and overall medical imaging environment. One example of an expanded functionality that may be provided by an external device is the execution of one or more machine learning (e.g., artificial intelligence) models on images or other DICOM objects stored on the medical image storage device. These AI models may be produced by any number of internal or external vendors and may be executed on one or more servers, referred to herein as AI orchestration platforms (AOPs) or AI servers, in communication with the medical image storage device.

The AOP is configured to execute one or more AI models against any given number of datasets (e.g., where the datasets are received from the medical image storage device). However, the AOP is not configured to persistently store the datasets or persistently store the results from the AI models. While such a configuration may allow for integration of multiple third-party AOPs while maintaining patient privacy and facilitating the production of rapid AI results, the AOPs thereby cannot provide any type of quality control workflow in the context of AI generated results. For example, the AOP may be integrated in a medical imaging system so that the AOP communicates exclusively with a medical image storage device, and may not communicate with any end user applications or other medical database systems (e.g., electronic medical record databases). The AOP may execute an AI model on a dataset (e.g., a plurality of medical images) obtained from the medical image storage device and send the results of the AI model back to the medical image storage device. When the results are viewed by an end user (e.g., clinician), if the end user does not agree with the results and thus rejects the results, the AOP may not be informed, as the AOP is only in communication with the medical image storage device, which is not configured to pass on any actions performed via the end user application, and thus the AOP is not able to refine or tune the AI model (or provide the end user feedback to the developer(s) of the AI models). Further, any objects that are generated by the AOP and sent to the medical image storage device (e.g., DICOM objects such as annotated images or images that have been processed to reduce image artifacts) may persist on the medical image storage device even if the results of the AI model have been rejected. Similar issues may apply when an end user performs actions that change an underlying dataset, such as performing an exam merge.

In addition, to be able to provide broad integration, many AOPs communicate with medical image storage devices by using DICOM C-Find queries for discovering new data via DICOM. C-Find queries can be expensive operations. Further, the queries also are restricted to whatever DICOM fields have been indexed in the medical image storage device's database, which can be limiting. Thus, due to the nature of the DICOM standard and limitations placed on medical image storage devices, current medical imaging systems may not execute quality control workflows, which may lead to invalidated AI results being saved at the medical image storage devices as well as lost opportunities for AI model tuning and refinement based on end user feedback.

The UAIS of the present disclosure aims to address the above issues by providing a workflow repository and engine between a medical image storage device (e.g., PACS or VNA) and an external server executing one or more AI models, such as an AOP, which allows the AOP to remain stateless and be manufactured by or configured by third-party vendors while also providing for feedback/quality control on the AI models stored on the AOP. The UAIS may be configured to communicate with multiple devices according to different communication protocols in order to notify an AOP that one or more images are available (e.g., having been sent to the medical image storage device from an imaging modality) so that the AOP may retrieve the one or more images from the medical image storage device, without requiring the AOP to perform a C-Find query of the medical image storage device. Further, the UAIS may be configured to receive the AI results from the AOP, persistently store the results, and communicate the results to one or more listeners or subscribers (e.g., an electronic medical record database). The UAIS may also monitor for end user actions that affect an AI result or change an underlying dataset on which a given AI result is based (e.g., rejection of AI results, changes to the dataset) and remove the AI result as well as any associated DICOM objects from the UAIS and the medical image storage device. When the end user provides feedback as to the quality of an AI result (e.g., reject or accept the results and any stated rationale), the end user feedback may be stored by the UAIS for presentation to the vendor that developed the AI model, so the AI model may be tuned or refined. In this way, a seamless workflow for executing one or more AI models may be achieved.

Figure 1:
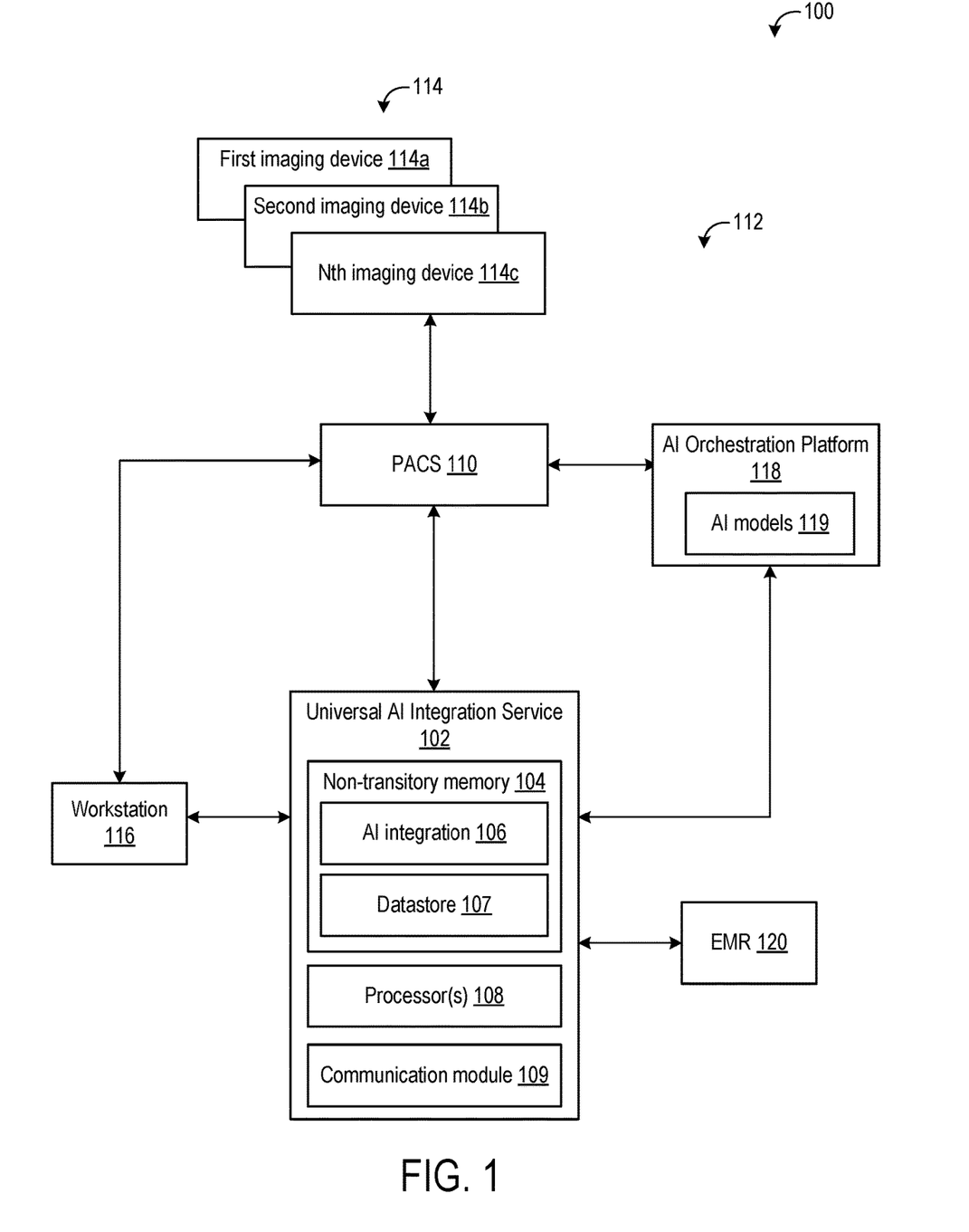
FIG. 1 schematically shows an example medical imaging system including a universal artificial intelligence (AI) integration service (UAIS) in communication with an AI orchestration platform (AOP).
Figure 2:
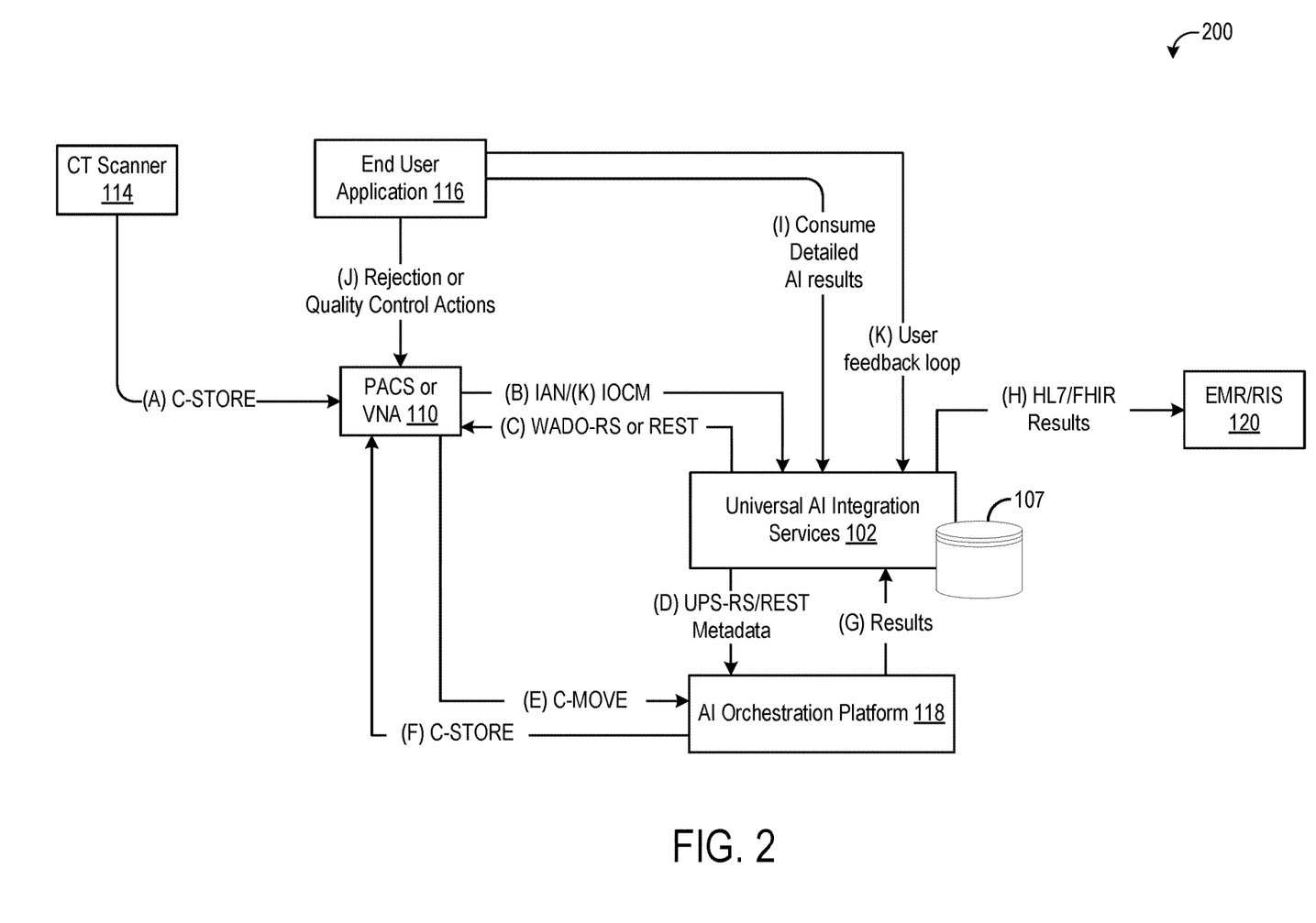
FIG. 2 schematically shows example communication occurring over the medical imaging system of FIG. 1.

FIG. 1 shows an example medical imaging environment in which a UAIS may be implemented in order to facilitate AI workflow management/integration between a medical image storage device and an AOP, according to the communication diagram of FIG. 2 and the methods of FIGS. 3-6.

FIG. 1 schematically shows an example medical imaging system 100 that may be implemented in medical facility such as a hospital. Medical imaging system 100 may include a plurality of medical imaging devices 114 each communicatively coupled to a picture archiving and communication system (PACS) 110. The plurality of medical imaging devices 114 includes a first imaging device 114a, a second imaging device 114b, and on up to an Nth imaging device 114c. The plurality of medical imaging devices 114 may include, as non-limiting examples, magnetic resonance imaging (MRI) devices, computed tomography (CT) devices, positron emission tomography (PET) devices, X-ray devices (including digital mammography devices, fluoroscopy devices, interventional devices, etc.), ultrasound devices, single-photon emission computerized tomography (SPECT) devices, and/or combinations thereof. As a non-limiting example, first imaging device 114a may be a CT device and second imaging device 114b may be an X-ray device.

Each medical imaging device may be configured to acquire medical images of a patient and send the acquired images to PACS 110 for long-term storage. PACS 110 may store the images and, when requested, may retrieve one or more images and send the retrieved images to one or more connected devices (as explained in more detail below). PACS 110 may obtain, store, and send images according to the DICOM standard. DICOM is the common standard for medical imaging and enumerates a command set, data formats, interface specifications, communication protocols, and command syntax. DICOM sets forth information objects (types of data, such as computerized tomography, magnetic resonance, x-ray, ultrasound, etc.), service classes (actions with data, such as send, receive, print, etc.), and data transmission protocols. DICOM application services provide the ability to transfer images and image related data between DICOM applications. A DICOM service-object pair (SOP) is used to push and/or pull information between DICOM applications.

PACS have a number of roles in data management. PACS receive image data sets fed from imaging devices and manage storage systems for data persistency, managing both short-term and long-term storage. PACS accept query requests from client applications, enabling those client applications to retrieve specified data. PACS may also interface with other healthcare information systems. Various devices may communicate with a PACS via the DICOM standard, such as medical imaging devices, workstations (e.g., workstation 116), radiology information service (RIS) devices, etc. While one PACS is shown in FIG. 1, it is to be appreciated that medical imaging system 100 may include more than one PACS, and may additionally or alternatively include one or more VNAs, which may be similar in function to PACS 110.

Medical imaging system 100 further includes an artificial intelligence (AI) orchestration platform (AOP) 118. The AOP 118 may store one or more AI models 119. For each AI model of the AI models 119, the AOP 118 may execute that AI model on one or more datasets (e.g., one or more images) received from PACS 110 in order to generate an AI result that is then sent to an external device (e.g., back to PACS 110), when indicated. For example, one of the AI models 119 may be configured to enter an X-ray image of a patient's lungs as input to the AI model and generate, as output, a finding related to the patient's lungs (e.g., presence or absence of pneumothorax). The AOP 118 may be configured as a stateless device, such that the datasets entered into the AI models 119 are not persistently saved on the AOP and the AI results that are output by the AI models 119 are not persistently saved on the AOP 118. For example, when a dataset is received from PACS 110, a session may be initiated between the PACS and the AOP. During the session, the dataset may be entered into one or more AI models on the AOP, and the AOP may generate AI results that are sent back to the PACS. Once the AI results have been sent, the session may be terminated and all session information (e.g., the dataset and AI results) may be deleted from temporary storage on the AOP. Further, while one AOP 118 is shown in FIG. 1, it is to be appreciated that more than AOP 118 may be included, with each AOP communicatively coupled to PACS 110.

Medical imaging system 100 further includes a universal AI integration service (UAIS) 102. UAIS 102 may include resources (e.g., memory 104, processor(s) 108) that may be allocated to store and execute an AI integration model 106 configured to control the workflows for executing the AI models 119 of the AOP 118. For example, the AI integration model 106 may direct the AOP to execute an AI model when a new dataset (e.g., one or more images) is sent to PACS 110 (e.g., from one of the imaging devices 114), receive the AI result from the AOP 118 upon the AI model being executed, save the AI result in a datastore 107 of the UAIS 102, send the AI result to one or more external listeners/subscribers, and orchestrate quality control/feedback by collecting end-user feedback on the AI results from the AI model and ensuring that prior AI results are removed from PACS 110 or updated when indicated (e.g., a dataset changes or an end user rejects an AI result).

UAIS 102 includes a communication module 109, memory 104, and processor(s) 108 to store and execute the AI integration model 106, as well as send and receive communications, graphical user interfaces, medical data, and other information. Communication module 109 facilitates transmission of electronic data within and/or among one or more systems. Communication via communication module 109 can be implemented using one or more protocols. In some examples, communication via communication module 109 occurs according to one or more standards (e.g., Digital Imaging and Communications in Medicine (DICOM), Health Level Seven (HL7), ANSI X12N, etc.). Communication module 109 can be a wired interface (e.g., a data bus, a Universal Serial Bus (USB) connection, etc.) and/or a wireless interface (e.g., radio frequency, infrared, near field communication (NFC), etc.). For example, communication module 109 may communicate via wired local area network (LAN), wireless LAN, wide area network (WAN), etc. using any past, present, or future communication protocol (e.g., BLUETOOTH™, USB 2.0, USB 3.0, etc.).

Memory 104 and/or datastore 107 may include one or more data storage structures, such as optical memory devices, magnetic memory devices, or solid-state memory devices, for storing programs and routines executed by processor(s) 108 to carry out various functionalities disclosed herein. Memory 104 and/or datastore 107 may include any desired type of volatile and/or non-volatile memory such as, for example, static random access memory (SRAM), dynamic random access memory (DRAM), flash memory, read-only memory (ROM), etc. Datastore 107 may persistently/permanently store AI results received from the AOP 118, such that the AI results are stored in the datastore 107 until a user commands the AI results be removed or deleted or until the UAIS 102 determines that a user has rejected the AI results. In this way, the AI results may be stored at the datastore 107 after a communication session with the AOP 118 has terminated. Processor(s) 108 may be any suitable processor, processing unit, or microprocessor, for example. Processor(s) 108 may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, UAIS 102 and PACS 110 are shown in FIG. 1 as each constituting a single entity, but it is to be understood that UAIS 102 and/or PACS 110 may be distributed across multiple devices, such as across multiple servers.

As shown in FIG. 1, a workstation 116 is shown communicatively coupled to UAIS 102 and PACS 110. Additional workstations may be present in medical imaging system 100, such as additional workstations associated with PACS 110, UAIS 102, and/or one or more of the plurality of imaging devices 114. Each workstation may include a processor, memory, communication module, user input device, display (e.g., screen or monitor), and/or other subsystems and may be in the form of a desktop computing device, a laptop computing device, a tablet, a smart phone, or other device.

While not specifically shown in FIG. 1, additional devices described herein (the plurality of imaging device 114, PACS 110, AOP 118, workstation 116) may likewise include user input devices, memory, processors, and communication modules/interfaces similar to communication module 109, memory 104, and processor(s) 108 described above, and thus the description of communication module 109, memory 104, and processor(s) 108 likewise applies to the other devices described herein. The user input devices may include keyboards, mice, touch screens, microphones, or other suitable devices.

UAIS 102 further communicates with the AOP 118 and an EMR database 120. As described above, the AOP 118 may be configured to store and execute one or more AI models 119. As such, AOP 118 may include user input devices, memory, processors, and communication modules/interfaces similar to communication module 109, memory 104, and processor(s) 108 described above, and thus the description of communication module 109, memory 104, and processor(s) 108 likewise applies to AOP 118.

EMR database 120 may be an external database via a secured hospital interface, or EMR database 120 may be a local database (e.g., housed on a device of the hospital). EMR database 120 may be a database stored in a mass storage device configured to communicate with secure channels (e.g., HTTPS and TLS), and store data in encrypted form. Further, the EMR database 120 is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

The devices shown in FIG. 1 may communicate directly and/or via a network 112. Further, in some examples, medical imaging system 100 may additionally include a vendor neutral archive (VNA), or medical imaging system 100 may include a VNA in place of PACS 110. Further still, while UAIS 102 is shown communicating with EMR 120, other databases or systems may communicate with UAIS 102, such as a radiology information system (RIS), a hospital information system (HIS), etc.

FIG. 2 shows an example workflow 200 occurring with system 100 relating to execution of an AI model stored on AOP 118, as orchestrated by the UAIS 102. An imaging device 114, such as a CT scanner, may obtain one or more medical images of a patient, which may be sent to PACS 110, as shown at step A. PACS 110 may save the images as part of a study or exam. The images may be DICOM images, and thus may include DICOM metadata that indicates patient information (e.g., name, date of birth, etc.), type of imaging device used to obtain the images, the anatomy being imaged, the type of study or exam, and so forth. As shown in FIG. 2, the images are sent using a C-Store function of the PACS 110.

Once the images are received at the PACS 110, the PACS 110 generates an instance availability notification (IAN) and sends the IAN to the UAIS 102, as shown at step B. The IAN indicates that new images have been saved to the PACS 110. When the UAIS 102 receives the IAN, the UAIS 102 determines if the IAN is relevant to the actions performed by the UAIS 102 (e.g., triggers an AI event). The PACS 110 (and/or a VNA, when included) may trigger IAN messages at any point in time and for a variety of reasons, some of which may be relevant for the AI related functions carried out by the UAIS 102, and some of which may not be relevant. For example, if there are patient updates that were received from a radiology information system (RIS), these updates may trigger an IAN message that is sent to the UAIS 102. However, that patient update (or any other action that triggers an IAN) may or may not be related to the actions performed by the UAIS, e.g., the patient update or other action may not demand that an AI model be executed or that AI results be rejected (as explained in more detail below). Thus, the UAIS 102 includes logic to determine if an IAN message should result in an AI event (delete or trigger). If the UAIS 102 determines that the IAN indicates new data (e.g., images) is available that could be entered into an AI model on the AOP, the UAIS 102 queries the PACS 110 for the DICOM metadata associated with the images and any relevant clinical information associated with the images and stored in the PACS 110, such as comments provided by a technologist during image acquisition. For example, as shown at step C, the UAIS 102 may perform a DICOMWeb WADO-RS or REST based query to the PACS 110. The PACS 110 then sends the DICOM metadata associated with the images to the UAIS 102, but does not send the images themselves to the UAIS 102.

The UAIS 102 starts a UPS-RS workitem with the AOP 118 for the given DICOM metadata, as shown at step D. Based on the DICOM metadata, an appropriate AI model stored on the AOP 118 may be selected to be executed on the images. For example, if the images are contrast-enhanced images of the brain obtained as part of a perfusion exam, an AI model trained to analyze the images in order to diagnose a stroke may be selected. The UAIS 102 may send the DICOM metadata to the AOP 118, and the AOP 118 may select the appropriate AI model to execute on the images.

Once the workitem has been initiated, the AOP 118 queries the PACS 110 to obtain the images, which are sent using a C-Move function as shown in step E. Depending on the AI model that is to be executed, all the images of the study may be requested, or only a subset of the images of the study may be requested. When the AOP 118 receives the images, the images may be entered as input to the selected AI model. Once the selected AI model generates an output (referred to as an AI result), the AOP 118 sends any generated DICOM objects (e.g., annotated images, text, measurements, etc.) to the PACS 110, shown by the C-Store function at step F. For example, if the output of the AI model includes an image with an annotation indicating a finding, the annotated image may be sent to the PACS 110. The AI result/generated DICOM objects are also sent to the UAIS 102 via the UPS-RS workitem, as shown by step G. The AI result may be stored in the datastore 107 of the UAIS 102.

The UAIS 102 may communicate the AI results to an EMR, RIS, and/or other subscriber, such as EMR 120, via one or more appropriate communication protocols, such as HL7 or FHIR if configured to do so, as shown by step H. By sending the AI results to the EMR or RIS, it makes the systems "connected" so that users can be alerted when AI results are available, rather than users having to poll the PACS to find if AI results are available. For example, if a dataset is entered into a stroke-related AI model, the AI results (e.g., indicating a diagnosis of stroke) would be critical in the EMR or RIS to provide rapid stroke protocol care.

An end user application, for example an application executing on workstation 116, may query the UAIS 102 for the entire AI results for a given study using a REST based API, as shown by step I. While not shown in FIG. 2, the UAIS 102 provides the entire AI results for the study to the end user application, e.g., for display on a display device of the workstation 116. Additionally, the end user application may also or alternatively query the PACS 110 for the AI results.

When an end user (e.g., clinician) reviews the AI results via the end user application on the workstation 116, the end user may evaluate the AI results and accept or reject the AI results. Further, the end user may review the images in the study and may make changes to the study, such as rejecting low quality images, merging multiple studies, or other changes. During one of these quality control actions, which are shown in FIG. 2 at step J, the AI results may be invalidated since the dataset used to generate the AI result has changed (e.g., images may be removed or added). If the AI results are invalidated, the AI results are removed from the PACS 110, which causes the PACS 110 to generate an Imaging Object Change Management (IOCM) message. The UAIS 102 listens for any IOCM messages from the PACS 110. Once an IOCM is received, the UAIS 102 may evaluate the message to see if it applies to any of the AI results stored in the datastore 107. If the message applies to any stored AI results, the UAIS 102 may proceed to reject the AI results (e.g., delete the results from the datastore 107) and then reject any DICOM objects in the PACS 110. The PACS may not be aware that the AI results (e.g., the generated DICOM objects) were generated by an AI model. To the PACS, the AI results are just more DICOM objects. However, the UAIS is aware that the generated DICOM objects are AI results and thus is configured to take the appropriate action when the AI results are rejected and/or the dataset upon which AI results are generated changes.

Further, the end user can tag the AI results if the end user agrees with the inferencing performed or the end user can reject the AI results. When the end user rejects the AI results, the end user may supply rationale as to why the end user rejected the AI results. These tags or rationale may be sent to the UAIS 102, as shown at step K, where the tags and rationale can be compiled and provided to the vendor who developed the AI model that generated the AI results, and later be used to refine the AI model.

Figure 3:
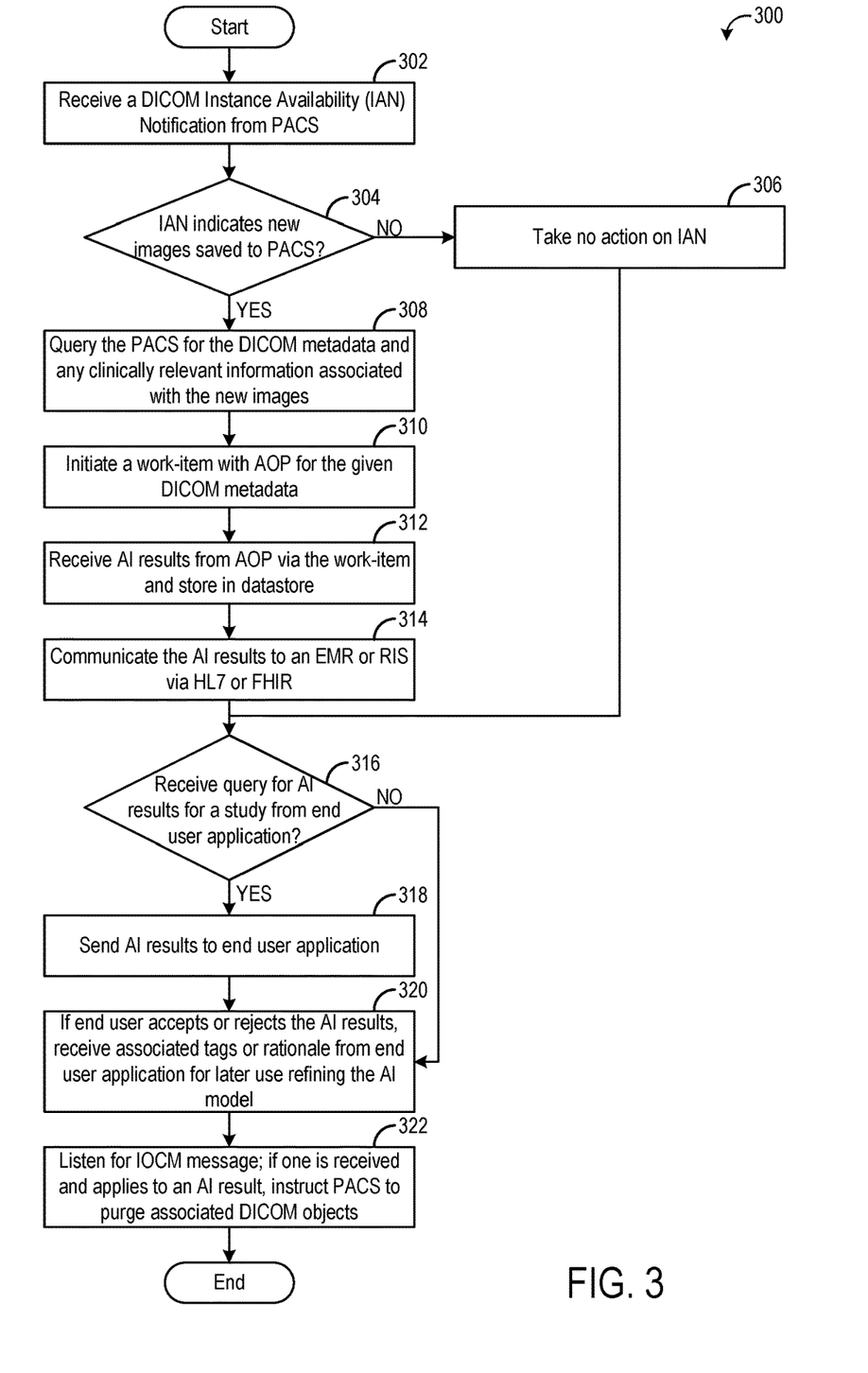
FIG. 3 is a flow chart illustrating an example method for AI workflow integration in a medical imaging system from a perspective of a UAIS of the medical imaging system.

FIG. 3 is a flow chart illustrating a method 300 for integrating AI workflows between a medical image storage device, such as a PACS, and an AI platform executing one or more AI models, such as an AOP. Method 300 may be implemented on a computing device in communication with a medical image storage device and AI platform, such as UAIS 102 in communication with PACS 110 and AOP 118. Method 300 may be executed by a processor of the computing device (such as processor(s) 108 of UAIS 102 of FIG. 1) according to instructions stored on a non-transitory memory of the device (e.g., memory 104 shown in FIG. 1).

Method 300 is described herein as being implemented by the medical imaging system 100 of FIGS. 1 and 2, but could be implemented in a different system, such as a medical imaging system including a VNA.

At 302, a DICOM instance availability notification (IAN) is received from a medical image storage device (e.g., PACS 110). The IAN indicates that an update has been made to/at the medical image storage device, such as new image(s) being saved to the medical image storage device, an exam/study being moved from one storage location to a different storage location, or an exam/study being removed from the medical image storage device. For example, upon completion of a CT scan, reconstructed images of a patient may be sent from a CT scanner to the PACS. Upon receiving the images, the PACS may generate an IAN and send the IAN to all connected devices that are configured to receive the IAN, including the UAIS. At 304, the UAIS determines if the IAN indicates that new images have been saved to the PACS. For example, the UAIS may be configured to read/parse the IAN message and determine if the IAN indicates new images have been saved, or if a different (e.g., not relevant) action has occurred at the PACS. If the UAIS determines that the IAN does not indicate new images have been saved to the PACS, method 300 proceeds to 306 to take no action on the IAN, and then method 300 proceeds to 316, described below. If the UAIS determines the IAN does indicate that new images have been saved to the PACS, method 300 proceeds to 308 to query the PACS for DICOM metadata and any clinically relevant information associated with the newly-stored images. For example, the IAN may include an identifier (e.g., unique identifier (UID)) identifying the study, series, etc. to which the newly-stored images belong, and the UAIS may query the PACS using a DICOM WADO-RS or a REST based query to get the DICOM metadata and any clinically relevant information. By configuring the UAIS to receive IANs rather than polling the PACS using a DICOM C-Find, the UAIS may operate more efficiently and any DICOM instances unknown to the UAIS may not be missed, which may occur if the UAIS (or AOP) were to poll the PACS using DICOM C-Find.

At 310, a workitem is initiated with an AOP (e.g., AOP 118) for the given DICOM metadata. The workitem may be a Unified Procedure Step (UPS-RS) workitem that specifies a task that is to be performed, herein that images are available for retrieval from the PACS and that the images are suitable for entering into one or more AI models executable by the AOP. The UPS-RS specification has provisions for the calling application (e.g., the UAIS) to poll or receive updates. Once the workitem has been completed, the UAIS will be aware that the workitem has been completed based on the UPS-RS specification and will retrieve the AI results from the AOP temporary endpoint. At 312, the UAIS receives AI results from the AOP via the workitem and stores the AI results in a datastore of the UAIS (e.g., datastore 107). The AI results may be the output from the one or more AI models executed by the AOP, using the images and, in some examples, other clinically relevant information as input. The AI results may include DICOM objects (e.g., images), free text, and/or other output from the AI model(s). At 314, the AI results are communicated to an EMR, a RIS, and/or other actors configured to receive information from the UAIS (e.g., entities that subscribe to notifications from the UAIS). The AI results may be communicated using HL7, FHIR, or another suitable protocol. Thus, once the AI results have been generated by the AI models and communicated to the UAIS, the AI results can be both persisted to the datastore and forwarded to any number of subscribers. These subscribers can be implementing any type of listening protocol and integrated directly with the UAIS by using the subscriber/adapter pattern. Some common communication use cases include communication of the AI results to an EMR or RIS via HL7 or FHIR, communication the of AI results to a PACS or VNA for minimal consumption in a worklist, and creation of DICOM objects based on the AI-generated results. For example, some DICOM viewers (e.g., end user application) may be configured to show an indicator on the user interface to tell the user that an image was generated by an AI model. The UAIS has the knowledge that the image was created by an AI model. Thus, when the end user application queries the UAIS, the end user application may be notified that the image was generated by an AI model as well.

The above-described process may be performed each time an IAN is received from the PACS, such that each time new images/a new study is saved to the PACS, the UAIS is notified and the UAIS directs the AOP to obtain the DICOM metadata to determine if the images/study is suitable for an AI model stored on the AOP. The UAIS receives the AI results from the AOP, stores the AI results, and communicates the AI results to all subscribers.

At 316, method 300 includes determining if a query has been received for the AI results for a given study (such as for the AI results received at 312) from an end user application (e.g., executing on a workstation, such as workstation 116). The end user application may be a DICOM viewer or another suitable application via which DICOM images may be viewed by an end user, such as a clinician. If a query requesting to view the AI results has been received, method 300 proceeds to 318 to send the AI results to the end user application for display. In this way, in response to the query, the AI results for the study may be retrieved from the datastore and displayed for viewing by the end user. If a query is not received, method 300 proceeds to 320. At 320, if the end user provides feedback as to any AI results (e.g., accepts or rejects the results, provides rationale on why the results were accepted or rejected), any associated tags (e.g., indicating if the results were accepted or rejected) and rationale are received from the end user application. The tags and rationale may be saved and provided to the developer/vendor that developed the AI model in order to tune or refine the AI model.

At 322, the UAIS listens for an Imaging Object Change Management (IOCM) message from the PACS. As explained above with respect to FIG. 2, an IOCM message may be generated by the PACS each time a DICOM object is changed or a study is updated by an end user. For example, the end user viewing a study (which may include AI results) via the end user application may opt to reject a low quality image included as part of the study, or may opt to merge two exams/imaging sessions together. These actions can result in a change to the dataset that was used to generate the AI results, making the AI results invalid. Thus, the UAIS may review the IOCM message to determine if the IOCM message indicates that any datasets upon which any AI results stored in the UAIS datastore have been changed. If the IOCM message applies to an AI result in the datastore, the UAIS may purge the affected AI result and instruct the PACS to purge any associated DICOM objects (e.g., images annotated with the AI results).

Thus, the UAIS provides for a feedback loop to enable AI models to be refined and remove AI results when the underlying dataset has changed. AI results are generated against a finite dataset. When an image is rejected or some other quality control function modifies the underlying dataset, the AI results are most likely invalid. For this reason, the AI results should be rejected and removed. However, not only the AI results should be rejected and removed, but any generated DICOM objects should be purged as well.

The Universal AI Integration Services listens for an IOCM message from the PACS or VNA to provide this type of workflow. Once an IOCM is received, the IOCM is evaluated to see if it applies to any of the AI results in the datastore. If it finds results, the UAIS will proceed to reject the AI results and then reject any DICOM objects in the PACS or VNA.

Figure 4:
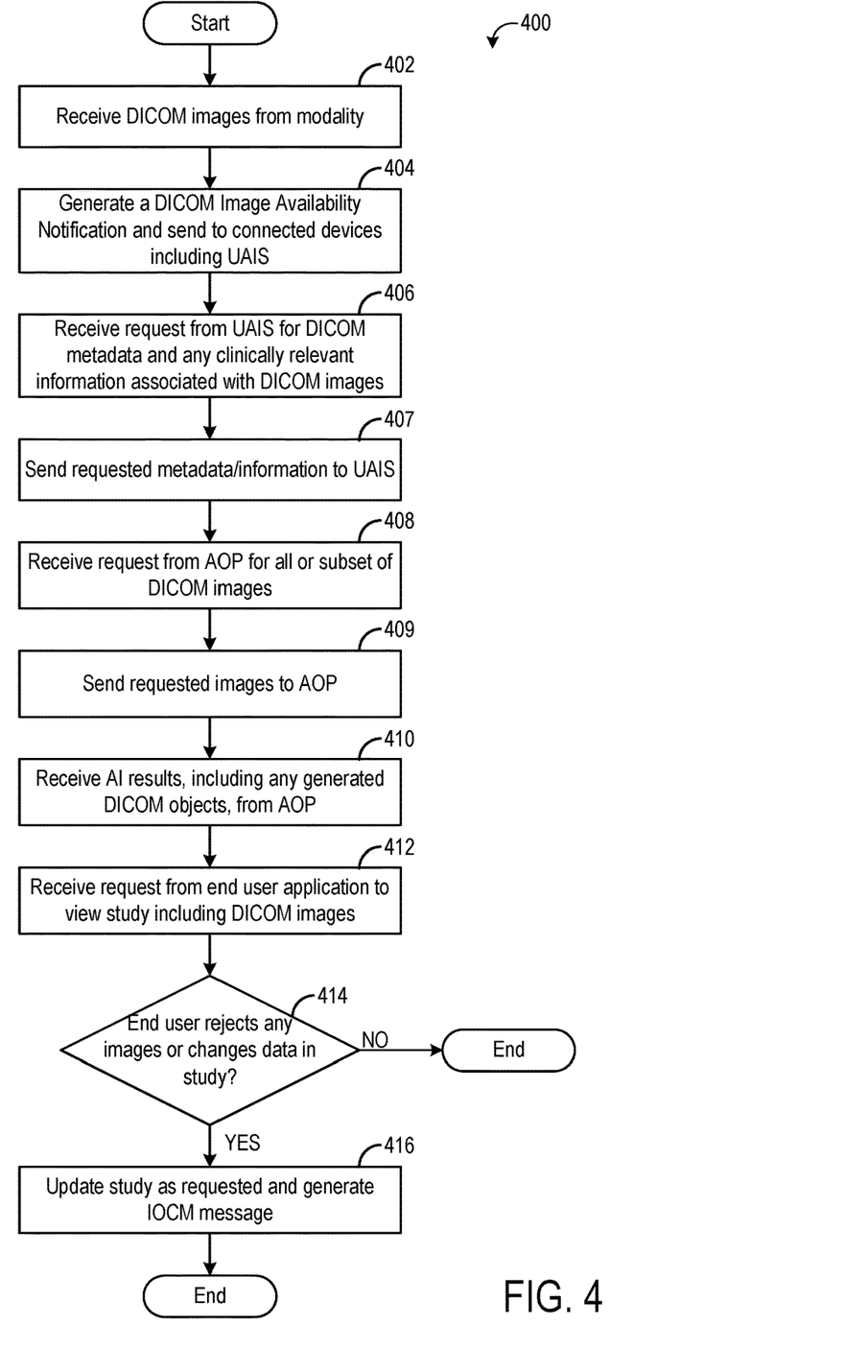
FIG. 4 is a flow chart illustrating an example method for AI workflow integration in a medical imaging system from a perspective of a PACS of the medical imaging system.

FIG. 4 illustrates a method 400 for integrating AI workflows between a medical image storage device, such as a PACS, and an AI platform executing one or more AI models, such as an AOP. Method 400 may be implemented on a DICOM/archive device in communication with a UAIS and AI platform, such as PACS 110. Method 400 may be executed by a processor of the computing device according to instructions stored on a non-transitory memory of the device. Method 400 is described herein as being implemented by the medical imaging system 100 of FIGS. 1 and 2, but could be implemented in a different system, such as a medical imaging system including a VNA. Method 400 may be carried out in parallel to method 300 of FIG. 3.

At 402, one or more DICOM images are received from an imaging modality. As explained above with respect to FIG. 3, the DICOM images may be acquired by the imaging modality (e.g., a CT scanner) and sent to the PACS for long-term storage. The DICOM images may be acquired as part of a study, and may include DICOM metadata, as explained above. At 404, a DICOM IAN is generated in response to receiving the DICOM images. The IAN is sent to any/all connected devices configured to receive IANs from the PACS, and thus the IAN is sent to the UAIS.

At 406, a request for DICOM metadata and any clinically relevant information associated with the DICOM images is received from the UAIS. At 407, in response to receiving the request for the metadata and other information, the DICOM metadata and any clinically relevant information associated with the images are sent to the UAIS. At 408, a request is received from an AOP (e.g., AOP 118) for all or a subset of the DICOM images. As explained above with respect to FIG. 3, once the UAIS receives the DICOM metadata, the UAIS may initiate a workitem with the AOP, and the AOP may in turn request the DICOM images (all of the images in the study, or a subset of the images in the study) from the PACS. Thus, at 409, the requested DICOM images are sent to the AOP. The AOP may execute one or more AI models on the DICOM images to generate AI results. At 410, the PACS receives the AI results, including any generated DICOM objects, from the AOP.

The above process may be repeated each time new images are saved to the PACS, such that an IAN is generated and sent to the UAIS, which in turn requests the DICOM metadata for the images referenced in the IAN. If the UAIS or AOP determines that an AI model is available to be executed on the images, the AOP may request the images or a subset of the images from the PACS and enter the images as input to the AI model. The AOP may then send the AI results to the PACS.

At 412, a request is received from an end user application to view a study (which includes DICOM images). The study may include the DICOM images that were received at 402, or the end user application may request to view a different study. In response to the request, the study/DICOM images may be output for display to an end user via the end user application. At 414, method 400 includes determining if an end user, via the end user application, has rejected any images in the study or otherwise changed any of the data in the study. If the end user has not rejected any images or made any changes to the data in the study, method 400 ends. If the user has rejected any images, merged any exams, or otherwise changed the data in the study, method 400 proceeds to 416 to update the study as requested (e.g., purge the rejected image) and generate an IOCM message. The IOCM message is sent to all subscribers, including the UAIS, as explained above with respect to FIG. 3. Method 400 then ends.

Figure 5:
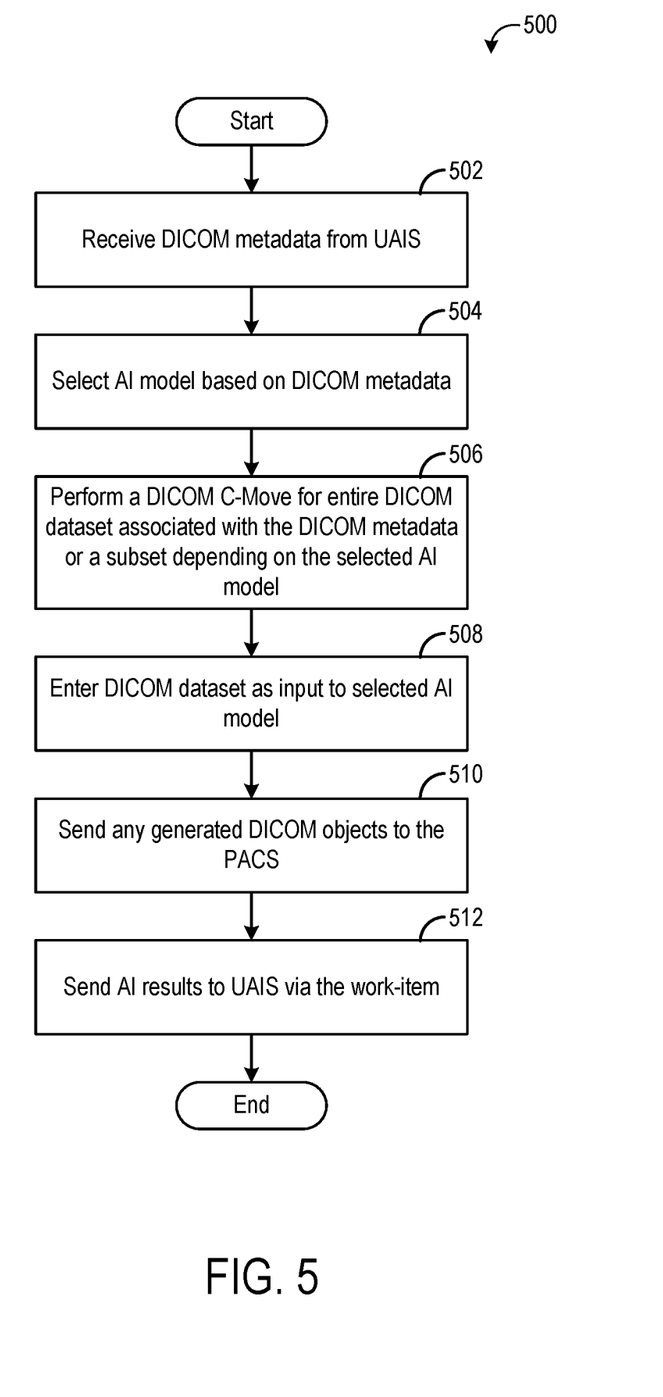
FIG. 5 is a flow chart illustrating an example method for AI workflow integration in a medical imaging system from a perspective of an AOP of the medical imaging system.

FIG. 5 illustrates a method 500 for integrating AI workflows between a medical image storage device, such as a PACS, and an AI platform executing one or more AI models, such as an AOP. Method 500 may be implemented on the AI platform, such as AOP 118. Method 500 may be executed by a processor of the computing device according to instructions stored on a non-transitory memory of the device. Method 500 is described herein as being implemented by the medical imaging system 100 of FIGS. 1 and 2, but could be implemented in a different system, such as a medical imaging system including a VNA. Method 500 may be carried out in parallel to method 300 of FIG. 3 and method 400 of FIG. 4.

At 502, DICOM metadata is received from a UAIS, such as UAIS 102. As explained above with respect to FIG. 3, when the UAIS is notified that new images have been saved to the PACS, the UAIS retrieves the DICOM metadata associated with the images and initiates a workitem with the AOP based on the DICOM metadata, where the workitem informs the AOP that images are available for entering into an AI model stored on the AOP. The UAIS may send the DICOM metadata to the AOP so that the AOP may determine which AI model should be executed and which images (if not all the images) are needed for executing the AI model. Thus, at 504, the AOP selects the appropriate AI model to execute based on the DICOM metadata.

At 506, the AOP queries the PACS (e.g., using a C-Move function) for the entire DICOM dataset (e.g., all the images) associated with the DICOM metadata, or for a subset of the dataset, depending on the selected AI model. The PACS may send the requested dataset to the AOP. At 508, the dataset received from the PACS is entered as input to the selected AI model. At 510, the AI results/generated DICOM objects output by the AI model are sent to the PACS. Likewise, at 512, the AI results are sent to the UAIS via the previously established workitem. In some examples, the AOP sends AI results in the form of DICOM objects to the PACS and sends AI results in the form of textual finding information to the UAIS, and thus the AI-related information that the AOP sends to the PACS may be different and/or in a different format than the AI-related information the AOP sends to the UAIS. The UAIS receives metadata information relating to the DICOM objects as well. In some examples, the AOP is a stateless device, and thus once the AI results have been generated and sent to the PACS and UAIS, the DICOM dataset and the AI results are deleted or otherwise not permanently stored on the AOP. Method 500 then ends.

Figure 6:
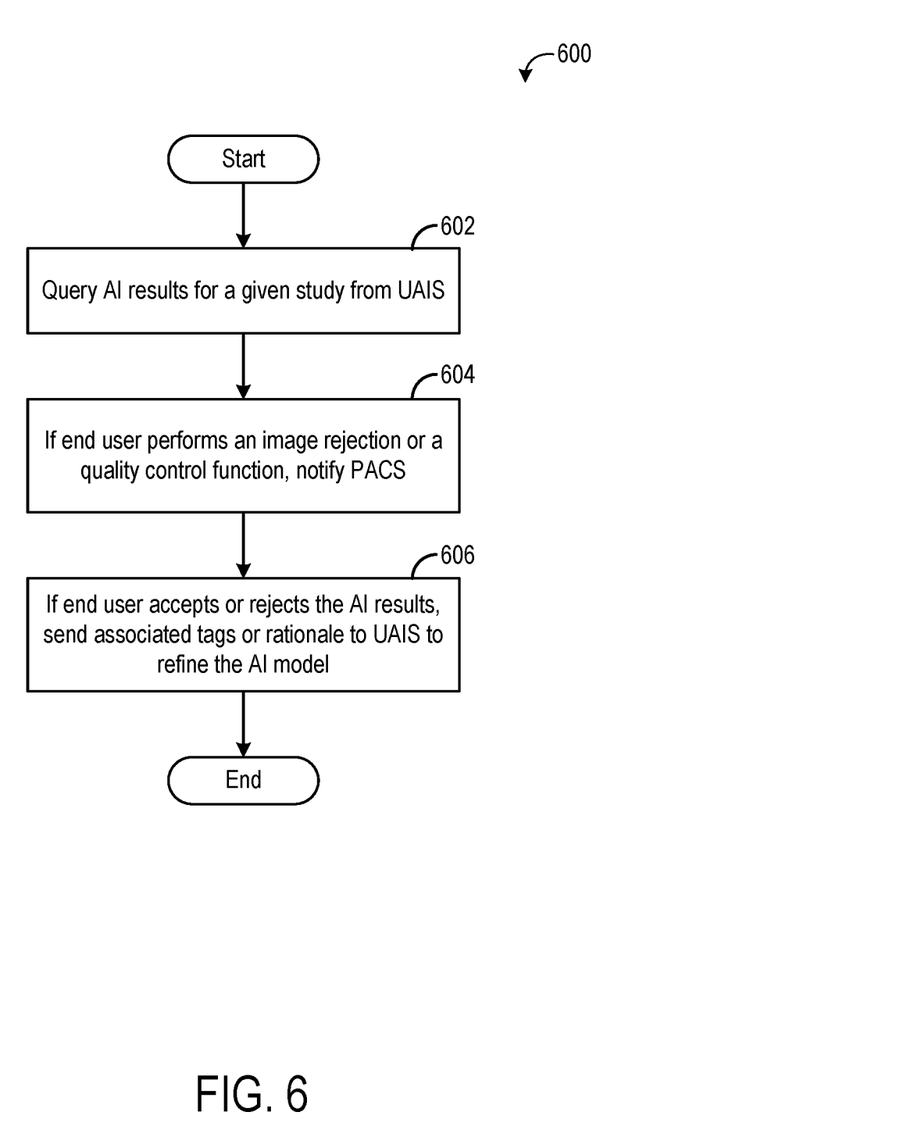
FIG. 6 is a flow chart illustrating an example method for AI workflow integration in a medical imaging system from a perspective of an end user application of the medical imaging system.

FIG. 6 illustrates a method 600 for integrating AI workflows between a medical image storage device, such as a PACS, and an AI platform executing one or more AI models, such as an AOP, via a UAIS. Method 600 may be implemented on a computing device executing an end user application, such as workstation 116. Method 600 may be executed by a processor of the computing device according to instructions stored on a non-transitory memory of the device. Method 600 is described herein as being implemented by the medical imaging system 100 of FIGS. 1 and 2, but could be implemented in a different system, such as a medical imaging system including a VNA. Method 600 may be carried out in parallel to method 300 of FIG. 3, method 400 of FIG. 4, and method 500 of FIG. 5.

At 602, in response to a user request, the AI results for a given study are queried from the UAIS. In response, the UAIS provides the AI results to be viewed by an end user via the end user application (e.g., a DICOM viewer). The query may be performed via a REST based API, at least in some examples. At 604, if the end user performs an image rejection or a quality control function on the study via the end user application (e.g., rejects an image), a notification is sent to the PACS. As explained above, the PACS may carry out the requested quality control function (e.g., purging the rejected image). At 606, if the end user accepts or rejects the AI results, any associated tags (e.g., indicating the results were rejected or accepted) and/or rationale (e.g., explaining why the results were accepted or rejected) are sent to the UAIS. As explained above, the tags and rationale may be provided to the AI model developer so that the tags and rationale can be used as feedback to tune, refine, or retrain the AI model. Method 600 then ends.

The disclosure also provides support for a method, comprising: receiving, from a medical image storage device, an instance availability notification, in response to determining that the notification indicates that one or more medical images have been saved at the medical image storage device, querying the medical image storage device to retrieve metadata associated with the one or more medical images, initiating a workitem with an artificial intelligence (AI) orchestration platform based on the metadata, and receiving, from the AI orchestration platform via the work-item, AI results related to the one or more medical images. In a first example of the method, the method further comprises: sending the AI results to an EMR or RIS via HL7 or FHIR. In a second example of the method, optionally including the first example, the method further comprises: receiving a request from an end user application for the AI results and sending the AI results to the end user application. In a third example of the method, optionally including one or both of the first and second examples, the method further comprises: receiving feedback regarding the AI results from the end user application. In a fourth example of the method, optionally including one or more or each of the first through third examples, the method further comprises: storing the feedback regarding the AI results for subsequent training of an AI model of the AI orchestration platform, wherein the AI model output the AI results. In a fifth example of the method, optionally including one or more or each of the first through fourth examples, the method further comprises: receiving, from an end user application, a notification that a user has rejected the one or more medical images, and discarding the AI results responsive to the notification. In a sixth example of the method, optionally including one or more or each of the first through fifth examples, the method further comprises: controlling the medical image storage device to discard any data objects related to the AI results stored at the medical image storage device.

The disclosure also provides support for a system, comprising: a medical image storage device communicatively coupled to a plurality of medical imaging devices, the medical image storage device configured to store medical images acquired via the plurality of medical imaging devices, an artificial intelligence (AI) server communicatively coupled to the medical image storage device, the AI server comprising a processor and a non-transitory memory storing a plurality of AI models, and an AI integration server communicatively coupled to the medical image storage device and the AI server, the AI integration server comprising a processor and a non-transitory memory storing a datastore for output of the plurality of AI models, the AI integration server configured with executable instructions stored in the non-transitory memory that when executed cause the processor to: receive, from the medical image storage device, an instance availability notification indicating that one or more medical images have been saved at the medical image storage device, retrieve, from the medical image storage device, metadata relating to the one or more medical images responsive to image availability notification, transmit, to the AI server, a request including the metadata relating to the one or more medical images, receive, from the AI server, AI results generated by one or more of the plurality of AI models for the one or more medical images, and store the AI results for the one or more medical images in the datastore. In a first example of the system, the instructions are further executable to send the AI results to an EMR or RIS via HL7 or FHIR. In a second example of the system, optionally including the first example, the instructions are further executable to receive a request from an end user application for the AI results and send the AI results to the end user application. In a third example of the system, optionally including one or both of the first and second examples, the instructions are further executable to receive feedback regarding the AI results from the end user application. In a fourth example of the system, optionally including one or more or each of the first through third examples, the instructions are further executable to store the feedback regarding the AI results for subsequent training of the one or more AI models. In a fifth example of the system, optionally including one or more or each of the first through fourth examples, the instructions are further executable to receive, from an end user application, a notification that a user has rejected the one or more medical images, and discard the AI results responsive to the notification. In a sixth example of the system, optionally including one or more or each of the first through fifth examples, the instructions are further executable to control the medical image storage device to discard any data objects related to the AI results stored at the medical image storage device.

The disclosure also provides support for a system, comprising: an AI integration server communicatively coupled to a medical image storage device and an AI server, the AI integration server comprising a processor and a non-transitory memory storing a datastore for output of a plurality of AI models stored on the AI server, the AI integration server configured with executable instructions stored in the non-transitory memory that when executed cause the processor to: receive, from the AI server, AI results generated by one or more of the plurality of AI models for one or more medical images stored at the medical image storage device, store the AI results for the one or more medical images in the datastore, receive, from an end user application, a notification that an end user has rejected the one or more medical images, and discard the AI results responsive to the notification, and control the medical image storage device to discard any data objects related to the AI results stored at the medical image storage device. In a first example of the system, the medical image storage device is communicatively coupled to a plurality of medical imaging devices and the medical image storage device is configured to store medical images acquired via the plurality of medical imaging devices, wherein the medical images are viewable by the end user via the end user application. In a second example of the system, optionally including the first example, the AI server is communicatively coupled to the medical image storage device and the AI server includes a processor and a non-transitory memory storing the plurality of AI models. In a third example of the system, optionally including one or both of the first and second example, the instructions are further executable to receive feedback regarding the AI results from the end user application. In a fourth example of the system, optionally including one or more or each of the first through third examples, the instructions are further executable to store the feedback regarding the AI results for subsequent training of the one or more AI models. In a fifth example of the system, optionally including one or more or each of the first through fourth examples, the AI server does not permanently store the AI results.

A technical effect of the universal AI integration services/server as disclosed herein is that quality control workflows may be performed on AI models in a DICOM environment. A further technical effect of the AI integration server as disclosed herein is that AI results may be communicated automatically to one or more listeners/subscribers, such as an EMR, which may allow clinicians to be informed of AI results rapidly and without undue user input. A still further technical effect is that an image storage device operating according to DICOM standard (e.g., a PACS) may be controlled/informed to remove invalidated AI results. Overall, the AI integration server may improve performance of the AI models, improve the efficiency of the PACS by removing invalidated AI results, and seamlessly integrate different actions of an AI workflow carried out by different devices in a medical imaging environment, while following DICOM standard.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method executable by an artificial intelligence (AI) integration server in communication with a medical image storage device, an AI orchestration platform, and at least one subscriber according to at least a first communication protocol for communicating with the medical image storage device and a second communication protocol for communicating with the at least one subscriber, the method comprising:

receiving, from the medical image storage device and according to the first communication protocol, an instance availability notification;

in response to determining that the notification indicates that one or more medical images have been saved at the medical image storage device, querying the medical image storage device to retrieve metadata associated with the one or more medical images;

receiving, from the medical image storage device, the metadata associated with the one or more medical images but not receiving the one or more medical images;

initiating a workitem with the AI orchestration platform based on the metadata;

receiving, from the AI orchestration platform via the workitem, AI results related to the one or more medical images;

permanently saving the AI results in a datastore of the AI integration server, wherein the AI orchestration platform temporarily stores the AI results and the AI results are removed from the AI orchestration platform once the AI results are sent to the AI integration server; and sending the AI results to the at least one subscriber according to the second communication protocol.

2. The method of claim 1, wherein the one or more images are DICOM images, the metadata is DICOM metadata, the AI results include a DICOM object, and the first communication protocol is a DICOM protocol, wherein receiving the instance availability notification comprises receiving the instance availability notification from the medical image storage device according to the DICOM protocol, wherein permanently saving the AI results in the datastore of the AI integration server comprises permanently saving the DICOM object in the datastore, and wherein the AI results received from the AI orchestration platform are different and/or in a different format than AI results that the AI orchestration platform sends to the medical image storage device.

3. The method of claim 1, wherein the second communication protocol is HL7 or FHIR, and wherein the at least one subscriber comprises one or more of an electronic medical record (EMR) database and a radiology information system (RIS).

4. The method of claim 1, further comprising receiving a request from an end user application for the AI results and sending the AI results to the end user application.

5. The method of claim 4, further comprising receiving feedback regarding the AI results from the end user application and storing the feedback regarding the AI results for subsequent training of an AI model of the AI orchestration platform, wherein the AI model outputs the AI results.

6. The method of claim 1, further comprising receiving, from an end user application, a second notification that a user has rejected the one or more medical images, and discarding the AI results responsive to the second notification.

7. The method of claim 6, further comprising controlling the medical image storage device to discard any data objects related to the AI results stored at the medical image storage device.

8. A system, comprising:

a medical image storage device communicatively coupled to a plurality of medical imaging devices, the medical image storage device configured to store medical images acquired via the plurality of medical imaging devices;

an artificial intelligence (AI) server communicatively coupled to the medical image storage device, the AI server comprising a processor and a non-transitory memory storing a plurality of AI models; and an AI integration server communicatively coupled to the medical image storage device and the AI server, the AI integration server comprising a processor and a non-transitory memory storing a datastore for output of the plurality of AI models, the AI integration server configured with executable instructions stored in the non-transitory memory that when executed cause the processor to:

receive, from the medical image storage device and according to a first communication protocol, an instance availability notification indicating that one or more medical images have been saved at the medical image storage device;

retrieve, from the medical image storage device, metadata relating to the one or more medical images but not retrieving the one or more medical images responsive to the instance availability notification;

transmit, to the AI server, a request including the metadata relating to the one or more medical images;

receive, from the AI server, AI results generated by one or more of the plurality of AI models for the one or more medical images;

permanently store the AI results for the one or more medical images in the datastore, wherein the AI server temporarily stores the AI results and the AI results are removed from the AI server once the AI results are sent to the AI integration server; and send the AI results to one or more subscribers via a second communication protocol.

9. The system of claim 8, wherein the metadata is DICOM metadata retrieved with a DICOMWeb WADO-RS or REST-based protocol.

10. The system of claim 8, wherein the instructions are further executable to receive a request from an end user application for the AI results and send the AI results to the end user application.

11. The system of claim 10, wherein the instructions are further executable to receive feedback regarding the AI results from the end user application.

12. The system of claim 11, wherein the instructions are further executable to store the feedback regarding the AI results for subsequent training of one or more AI models of the plurality of AI models.

13. The system of claim 8, wherein the instructions are further executable to receive, from an end user application, a notification that a user has rejected the one or more medical images, and discard the AI results responsive to the notification.

14. The system of claim 13, wherein the instructions are further executable to control the medical image storage device to discard any data objects related to the AI results stored at the medical image storage device.

15. A system, comprising:

an artificial intelligence (AI) integration server communicatively coupled to a medical image storage device and an AI server storing a plurality of AI models, the AI integration server comprising a processor and a non-transitory memory storing a datastore for output of the plurality of AI models, the AI integration server configured with executable instructions stored in the non-transitory memory that when executed cause the processor to:

receive, from the AI server, AI results generated by one or more of the plurality of AI models for a dataset including one or more medical images stored at the medical image storage device;

store the AI results for the one or more medical images in the datastore, wherein the AI server temporarily stores the AI results and the AI results are removed from the AI server once the AI results are sent to the AI integration server;

receive, from the medical image storage device, an imaging object change management (IOCM) message, wherein the IOCM message is generated by the medical image storage device in response to a change, by an end user, to data stored on the medical image storage device; and determine, from the IOCM, that the dataset used to generate the AI results has been changed and thus the AI results are invalid, and, in response, discard the AI results stored in the datastore and control the medical image storage device to discard any data objects related to the AI results stored at the medical image storage device.

16. The system of claim 15, wherein the medical image storage device is communicatively coupled to a plurality of medical imaging devices and the medical image storage device is configured to store medical images acquired via the plurality of medical imaging devices, and wherein the medical images are viewable by the end user via an end user application.

17. The system of claim 15, wherein the AI server is communicatively coupled to the medical image storage device and comprises a processor and a non-transitory memory storing the plurality of AI models.

18. The system of claim 15, wherein the instructions are further executable to receive feedback regarding the AI results from an end user application.

19. The system of claim 18, wherein the instructions are further executable to store the feedback regarding the AI results for subsequent training of one or more AI models of the plurality of AI models.

* * * * *